United States Patent
Castro et al.

(10) Patent No.: US 7,425,645 B2
(45) Date of Patent: Sep. 16, 2008

(54) ESTER-LINKED GEMINI SURFACTANT COMPOUNDS FOR USE IN GENE THERAPY

(75) Inventors: Mariano Javier Castro, Cambridge (GB); Christopher Kitson, Stevenage (GB); Mark Ladlow, Cambridge (GB); Alpesh Patel, Cambridge (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/815,570

(22) PCT Filed: Feb. 3, 2006

(86) PCT No.: PCT/EP2006/000998

§ 371 (c)(1),
(2), (4) Date: Aug. 6, 2007

(87) PCT Pub. No.: WO2006/082088

PCT Pub. Date: Aug. 10, 2006

(65) Prior Publication Data

US 2008/0058279 A1    Mar. 6, 2008

(30) Foreign Application Priority Data

Feb. 7, 2005    (GB) ................. 0502482.3

(51) Int. Cl.
*C07C 229/00* (2006.01)
*C12N 15/00* (2006.01)
*C12N 15/18* (2006.01)
*C12N 15/74* (2006.01)

(52) U.S. Cl. .............. 560/155; 560/169; 560/171; 435/455; 435/468; 435/471

(58) Field of Classification Search .......... None
See application file for complete search history.

(56) References Cited

U.S. PATENT DOCUMENTS 5,565,290 A    10/1996 Itakura et al.
2003/0229037 A1    12/2003 Ulrich et al.

FOREIGN PATENT DOCUMENTS

| WO | WO 95/11693 A | 5/1995 |
| WO | 9527705 | * 10/1995 |
| WO | WO 95/27705 A | 10/1995 |
| WO | WO 2004/087656 | 10/2004 |

OTHER PUBLICATIONS

Rioselle et al., Journal of Controlled Release 51 (1998) 131-142.*
Couchet et al., Tetrahedron Letters (2003), 44(26), 4869-4872.*
Kraemer et al., ChemBioChem (2004), 5(8), 1081-108.*
Rao Weisun, et al. "Spermic acid Diester Derivatives as pharmacological carriers for long-term controlled nitric oxide delivery." *Chemical and Pharmaceutical Bulletin* Vo. 46, No. 11, pp. 1846-1847, Nov. 1998.

(Continued)

*Primary Examiner*—Karl J Puttlitz

(74) *Attorney, Agent, or Firm*—Reid S. Willis; William Majarian; Stephen Venetianer

(57) ABSTRACT

This invention relates to newly identified ester-linked Gemini surfactant compounds of formula (I), where Y is either H or (Aa)x where (Aa) is a basic amino acid and x is 1 to 6, to the use of such compounds and to their production. The invention also relates to the use of the ester-linked Gemini surfactant compounds to facilitate the transfer of polynucleotide into cells.

12 Claims, 7 Drawing Sheets

OTHER PUBLICATIONS

Roselle D. C., et al., "Characterization and nitric oxide release studies of lipophilic I-substituted diazen-1-ium-1, 2-diolates." *Journal of controlled Release, Elsevier, Amsterman*, NL. vol. 51, No. 2-3, pp. 131-142, Feb. 12, 1998.

Kaluderovic, Goran N., et al. "Synthesis and characterization of the cobalt (III) complexes with ethylenediamine-N, N'-di-3-propanoate ligand and its esters." *Polyhedron*, vo. 21, No. 22, pp. 2277-2282.

Locastro S.M., et al., "The synthesis of a hematoregulatory agent based on HP-5B containing an effective, achiral cystine replacement." *Bioorganice & Medicinal Chemistry Letters*, Oxford, GB., vol. 6, No. 22, pp. 2709-2712, Nov. 19, 1996.

Lee, Tzu-Ming et al., "Physicochemical characterization of the dimeric lanthanide complexes [en{Ln(DO3A)(H20){2] and [pi{Ln(DTTA)(H20){2]2-: A variable-temperature 170 NMR study." *Magnetic Resonance in Chemistry*, vol. 41, No. 3, pp. 329-336.

Sinkin, Robert A., et al. "The synthesis of derivatives of 3, 7-diazanonanedioic acid." *Journal of Chemical and Engineering Data*, vol. 22, No. 2, pp. 237-238.

Hook, R.j., et al. Synthesis of polyamine-linked bis-daunomycin hydrazones and their interaction with DNA, *Anti-Cancer Drug Design*, vol. 4, No. 3, pp. 173-190 (1989).

Fisicaro, et al., "Biologically active bisquaternary ammonium chlorides: physico-chemical properties of long chain amphiphiles and their evaluation as non-viral vectors for gene delivery.", *BBA-general Subjects, Elsevier Science Publishers*, NL, vol. 1722, No. 2, Jan. 19, 2005.

* cited by examiner

ESTER-LINKED GEMINI SURFACTANT COMPOUNDS FOR USE IN GENE THERAPY

This invention relates to newly identified ester-linked surfactant compounds, to the use of such compounds and to their production. The invention also relates to the use of the ester-linked surfactant compounds to facilitate the transfer of compounds into cells for drug delivery. Compounds with properties related to properties of compounds of the invention are often referred to as Gemini surfactants.

Surfactants are substances that markedly affect the surface properties of a liquid, even at low concentrations. For example surfactants will significantly reduce surface tension when dissolved in water or aqueous solutions and will reduce interfacial tension between two liquids or between a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega, Y et al., *Kolloidn. Zh.* 36, 649, 1974). These molecules, which have been termed "gemini" (Menger, F M and Littau, C A, *J. Am. Chem. Soc.* 113, 1451, 1991), have very desirable properties over their monomeric equivalents. For example they are highly effective in reducing interfacial tension between oil and water based liquids and have a very low critical micelle concentration (Nenger, F M and Keiper, J S, *Angewandte. Chem. Int. Ed. Engl.,* 2000, 39, 1906).

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. WI, USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao, X et al. *Gene Ther.* 2, 710-722, 1995 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., *Nature Medicine,* 1, 39-46, 1995). More recently other groups have investigated the potential of other cationic lipids for gene delivery (Miller, A, *Angew. Int. Ed. Engl.,* 37, 1768-1785, 1998), for example cholesterol derivatives (Oudrhiri, N et al. *Proc. Natl. Acad. Sci.* 94, 1651-1656, 1997). This limited study demonstrated the ability of these cholesterol based compounds to facilitate the transfer of genes into epithelial cells both in vitro and in vivo, thereby lending support to the validity of this general approach.

The use of non-viral (cationic lipid) vectors for gene transfection has recently been reviewed, see D. Niculescu-Duvaz, J. Heyes and C. J. Springer, *Curr. Med. Chem.,* 2003, 10, 1233.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. Gemini surfactants based on cysteine (WO99/29712) or on spermine (WO00/77032) or diamine (WO00/76954) have previously been made. Other examples of gemini surfactants are found in WO00/27795, WO02/30957, WO02/50100, WO03/82809, GB0425555.0 and GB0425556.8. The use of Gemini surfactants as polynucleotide vectors has recently been reviewed (A. J. Kirby, P. Camilleri, J. B. F. N. Engberts, M. C. Feiters, R. J. M. Nolte, O. Söderman, M. Bergsma, P. C. Bell, M. L. Fielden, C. L. García Rodríguez, Philippe Guédat, A. Kremer, C. McGregor, C. Perrin, G. Ronsin and M. C. P. van Eijk, *Angew. Chem. Int. Ed.,* 2003, 42, 1448, see also R. Zana and J. Xia, *Gemini Surfactants*, Marcel Dekker, NY, 2004).

A recently developed technique involves the use of synthetic short interfering (si) double stranded RNA molecules to transiently suppress gene function. This technique of RNA interference (RNAi), originally coined from work in *C. elegans* (A. Fire, Trends Genet., 1999, 15(9), 358) was later developed such that its use could be applied to mammalian cells (S. M. Elbashir, J. Harborth, W. Lendeckel, A. Yalcin, K. Weber, T. Tuschl, Nature, 2001, 411, 494). The ability to deliver these siRNA effector molecules to the correct location of the majority of a cell population is a key step in the effective utilisation of this technology. Once correctly localised the antisense strand of the RNA duplex binds to the complementary region of the targeted messenger (m)RNA (coding for the target of interest), leading to hydrolysis of the mRNA and its subsequent degradation. This transient reduction in mRNA leads to a transient reduction in target gene expression. Highly efficient delivery and correct localisation are required to reduce target gene expression to levels such that the function of the target can be elucidated.

The present invention seeks to improve upon the properties of existing compounds.

The invention relates to compounds having the general structure of formula (I):

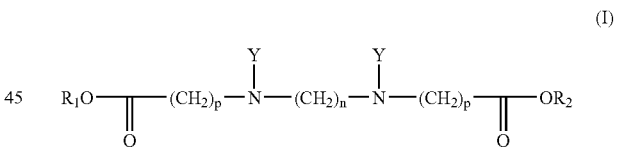

where Y is either H or $(Aa)_x$ where (Aa) is a basic amino acid and x is 1 to 6;

$R_1$ and $R_2$, which may be the same or different, is a saturated or unsaturated, linear or branched hydrocarbon chain of up to 24 carbon atoms;

n is 1 to 10; and p is 1 to 6;

or a pharmaceutically acceptable salt thereof.

In a preferred embodiment the $R_1$ or $R_2$ saturated or unsaturated, linear or branched hydrocarbon chain of up to 24 carbon atoms has 10 or more carbon atoms, for example 12 or more, for example 14 or more, for example 16 or more carbon atoms. In a further preferred embodiment the $R_1$ or $R_2$ saturated or unsaturated, linear or branched hydrocarbon chain of up to 24 carbon atoms is selected from:

—$(CH_2)_{10}CH_3$
—$(CH_2)_{12}CH_3$
—$(CH_2)_{14}CH_3$

—$(CH_2)_{16}CH_3$
—$(CH_2)_{18}CH_3$
—$(CH_2)_{20}CH_3$
—$(CH_2)_7CH$=$CH(CH_2)_7CH_3$ natural mixture
—$(CH_2)_7CH$=$CH(CH_2)_5CH_3$ natural mixture
—$(CH_2)_7CH$=$CH(CH_2)_5CH_3$ Cis
—$(CH_2)_7CH$=$CH(CH_2)_7CH_3$ Cis
—$(CH_2)_7CH$=$CH(CH_2)_5CH_3$ Trans
—$(CH_2)_7CH$=$CH(CH_2)_7CH_3$ Trans
—$(CH_2)_7CH$=$CHCH_2CH$=$CH(CH_2)_4CH_3$
—$(CH_2)_7(CH$=$CHCH_2)_3CH_3$
—$(CH_2)_3CH$=$CH(CH_2CH$=$CH)_3(CH_2)_4CH_3$
—$(CH_2)_7CHCH(CH_2)_7CH_3$
—$CH_2CH(CH_3)[CH_2CH_2CH_2CH(CH_3)]_3CH_3$
or —$(CH_2)_{22}CH_3$.

Most preferably the hydrocarbon chain is selected from $(CH_2)_7CH$=$CH(CH_2)_7CH_3$ natural mixture, $(CH_2)_7CH$=$CH(CH_2)_7CH_3$ Cis and $(CH_2)_7CH$=$CH(CH_2)_7CH_3$ Trans.

Preferably n is 3 to 6. Most preferably n is 4.
Preferably p is 1 to 4. Most preferably p is 2.
Y is preferably (Aa).

$(Aa)_x$, which may be the same or different at each occurrence, is x natural or unnatural amino acids linked in a linear or branched manner; (Aa) is a basic amino acid, preferably L or D enantiomers of serine (ser), lysine (lys), ornithine (orn), diaminobutyric acid (dab) or diaminopropionic acid (dap).

x is 1 to 6; preferably 1 to 3. Most preferably x is 1.

The group (Aa) is linked to the N in formula (I) by means of a peptide (amide) bond between the N and the carboxy group on the amino acid residue.

In one embodiment, a compound of the invention is a so-called 'Gemini' surfactant compound. That is to say that the compound is symmetrical in that each Y is the same and $R_1$ and $R_2$ are the same. In the context of the present invention such compounds are termed "ester geminis".

In a most preferred embodiment the ester gemini is selected from the group consisting of:

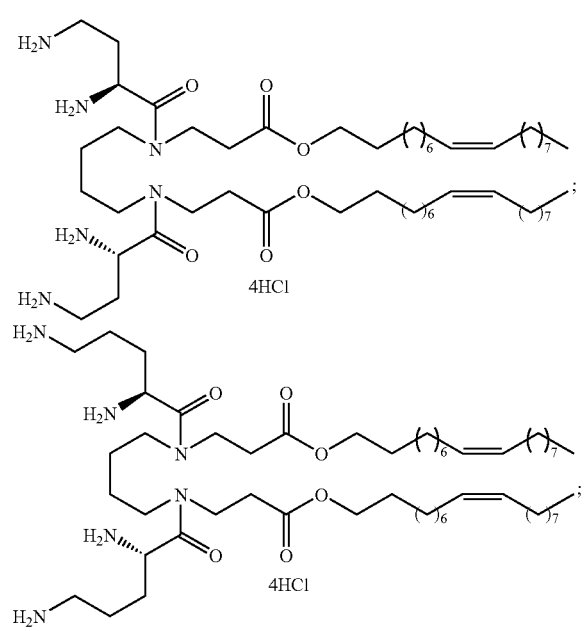

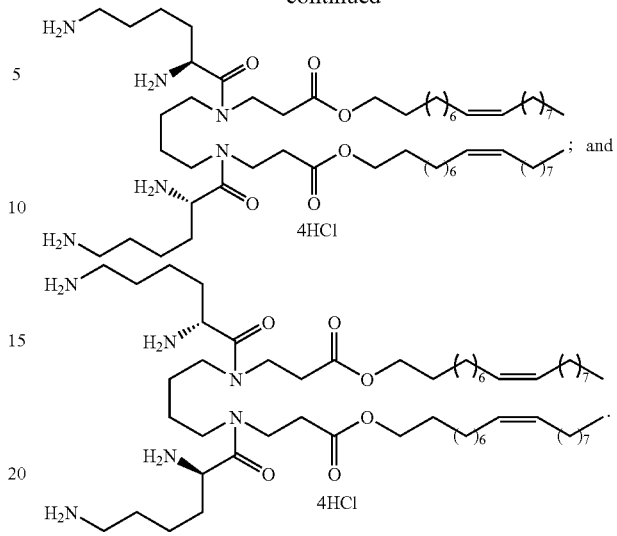

Compounds of the present invention may be prepared from readily available starting materials using synthetic chemistry well known to the skilled person. FIG. 1 shows a general scheme for the synthesis of preferred compounds of the invention where p=2. For compounds where p=1 or 3 to 6 other dicarboxylic acids (intermediate 3 in FIG. 1) may be used as starting materials using techniques well known in the art, for example Jaine, N et al.; Journal of Inorganic Biochemistry 1994, 53(2), 79-94 for where p=1; Reppe et al.; JLACBF; Justus Liebigs Ann. Chem.; 596; 1955; 1,215 for where p=3 and Gautier; Renault; Recl. Trav. Chim. Pays-Bas; 69; 1950; 421, 426 for where p=4.

Various alternative strategies are well known to the skilled person and suitable strategies may be devised for any particular desired final substitution pattern. For asymmetric substitution patterns, physical separation of products or intermediates may be necessary. Suitable separation methods, for example chromatographic methods, are well known to the person skilled in the art.

Salts of molecules in accordance with the invention may be prepared by standard techniques.

Another aspect of the invention relates to methods for using the ester-linked surfactant compounds. Such uses include facilitating the transfer of oligonucleotides and polynucleotides into cells for antisense, gene therapy and genetic immunisation (for the generation of antibodies) in whole organisms. Other uses include employing the compounds of the invention to facilitate the transfection of polynucleotides into cells in culture when such transfer is required, in, for example, gene expression studies and antisense control experiments among others. Protocols for the preparation of such polynucleotides and antisense molecules are well known in the art (for example Sambrook et al., Molecular Cloning: A Laboratory Manual, 2nd Ed., Cold Spring Harbor Laboratory Press, Cold Spring Harbor, N.Y. (1989), Cohen, J S ed. Oligodeoxynucleotides as Antisense Inhibitors of Gene Expression, CRC Press, Boca Raton, Fla. (1989)). The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqman® method (Perkin Ehner, Connecticut, USA). Compounds of the invention offer a significant improvement, typically between 3 and 6 fold, in the efficiency of cellular uptake of DNA in cells in culture, compared with compounds in the previous art. In the transfection protocol, the spermidine surfactant compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta,* 1235-1289);

(ii) a complexing reagent, for example the commercially available PLUS reagent (Life Technologies Inc. Maryland, USA) or peptides, such as polylysine or polyornithine peptides or peptides comprising primarily, but not exclusively, basic amino acids such as lysine, ornithine and/or arginine. The list above is not intended to be exhaustive and other supplements that increase the efficiency of transfection are taken to fall within the scope of the invention.

In still another aspect, the invention relates to the transfer of genetic material in gene therapy using the compounds of the invention. For example the skilled person can develop gene delivery methodologies for use in gene therapy, involving the use of spermidine surfactant compounds of the present invention, using protocols that are well known in the art. For example the use of surfactants for delivery of gene transfer vectors to the lung is reviewed in Weiss, D J (2002) Molecular Therapy 6(2) pp148 to 152.

Yet another aspect of the invention relates to methods to effect the delivery of non-nucleotide based drug compounds into cells in vitro and in vivo using the compounds of the invention.

The following definitions are provided to facilitate understanding of certain terms used frequently herein.

"Amino acid" refers to dipolar ions (zwitterions) of the form $^+H_3NCH(R)CO_2^-$. They are differentiated by the nature of the group R, and when R is different from hydrogen can also be asymmetric, forming D and L families. There are 20 naturally occurring amino acids where the R group can be, for example, non-polar (e.g. alanine, leucine, phenylalanine) or polar (e.g. glutamic acid, histidine, arginine and lysine). In the case of unnatural amino acids R can be any other group which is not found in the amino acids found in nature.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single-and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNA's or RNA's containing one or more modified bases and DNA's or RNA's with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL,* 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, trifluoroacetic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, trifluoroacetate, benzenesulfonate, methanesulfonate, ethanesulfonate, naphthalenesulfonate (e.g. 2-naphthalenesulfonate) or hexanoate salt.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The invention will now be described by way of the following examples. The examples are not to be taken in any way to limit the scope of the invention.

EXAMPLES

Description 1:
N,N'-Bis-(2-cyanoethyl)-1,4-diaminobutane (2)

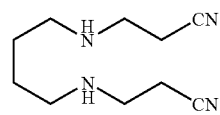

To a solution of 1,4-diaminobutane 1 (n=4; 25.0 g, 0.28 mol) in methanol (50 mL) was added dropwise a solution of acrylonitrile (31.6 g, 0.60 mmol) in methanol (25 mL) at 0° C. After the addition the mixture was allowed to come to room temperature and then stirred for 18 h. Finally, the solvent was removed in vacuo, to give the diamine 2 as a pale yellow liquid, (57.0 g, quant.).

Rf$_{Silica}$: 0.60 (MeOH-0.88NH$_3$ 95:5). $^1$H-NMR (CDCl$_3$): $\delta_H$2.88 (m, 4H), 2.60 (m, 4H), 2.46 (m, 4H), 1.45 (m, 4H).

Description 2: N,N'-Bis-(2-carbethoxyethyl)-1,4-diaminobutane dihydrochloride (3)

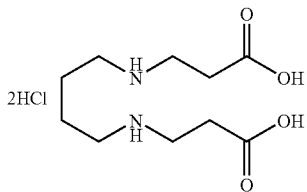

A solution of 2 (n=4; 10.0 g, 51.5 mmol) in 6N HCl (80 mL) was heated at reflux for 18 h, then allowed to cool to room temperature and the solvent partially evaporated in vacuo. To the residual solution was added EtOH (40 mL) and the precipitated solid was filtered off and washed with EtOH (10 mL) to afford the di-carboxylic acid 3 as a white solid (17.4 g, quant.).

$^1$H-NMR (d$^6$ DMSO): $\delta_H$ 12.70 (brs, 2H), 3.05 (t, J=7.5, 4H), 2.88 (m, 4H), 2.72 (t, 4H), 1.65 (m, 4H).

Description 3: N,N'-Bis-(2-carbethoxyethyl)-N,N'-bis-(tert-butoxycarbonyl)-1,4-diaminobutane (4)

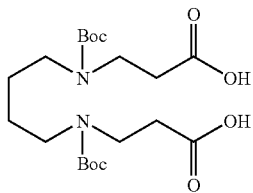

To a solution of 3 (n=4; 19.9 g, 65.3 mmol) in 1N NaOH (350 mL) was added a solution of di-tert-butyl dicarbonate (57.0 g, 261 mmol) in dioxane (350 mL). The mixture was stirred at rt for 18 h, and then concentrated to half volume The residue was adjusted to pH 3-4, and then extracted with dichloromethane (250 mL×3). The combined organic extracts were washed with brine (150 mL), dried (Na$_2$SO$_4$) and concentrated in vacuo to leave the carbamate 4 as a white powder (24.4 g, 87%).

Rf$_{Silica}$: 0.31 (EtOAc-MeOH 2:1). LC-MS (ESI): t$_R$=4.04 min (m/z=433.1 [M+H$^+$]).

Description 4: 3-(tert-Butoxycarbonyl-{4-[tert-butoxycarbonyl-(2-octadec-8-enyloxycarbonyl-ethyl)-amino]-butyl}-amino)-propionic acid octadec-8-enyl ester (5)

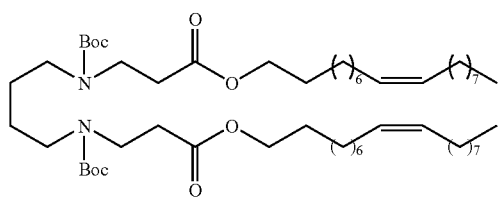

To a solution of the N-protected amino acid 4 (n=4; 15.2 g, 35.1 mmol), dimethylaminopyridine (1.70 g, 14.0 mmol) and oleyl alcohol (18.4 g, 68.4 mmol) in dichloromethane (200 mL) was added a solution of EDCI (13.1 g, 68.4 mmol), in dichloromethane (50 mL) at 0° C. The resulting mixture was allowed to warm to room temperature and then stirred under N$_2$ for 18 h. Dichloromethane (250 mL) was added and the mixture was washed with brine (4×200 mL), dried (Na$_2$SO$_4$) and concentrated in vacuo to leave an oil which was purified by column chromatography eluting with a solvent gradient of CH$_2$Cl$_2$ (50-90%) in hexane to afford the ester 5 as a colourless oil (13.0 g, 40%).

Rf$_{silica}$: 0.61 (Hex-EtOAc 7:3). $^1$H-NMR (CDCl$_3$): $\delta_H$ 5.32 (m, 4H), 4.05 (t, J=7.0, 4H), 3.42 (brs, 4H), 3.18 (brs, 4H), 2.53 (brs, 4H), 1.98 (m, 8H), 1.60 (m, 6H), 1.42 (m, 22H), 1.40-1.20 (m, 40H), 0.86 (t, J=7.0, 6H).

Description 5: 3-[4-(2-Octadec-9-enyloxycarbonyl-ethylamino)-butylamino]-propionic acid octadec-9-enyl ester bis hydrochloride salt (6)

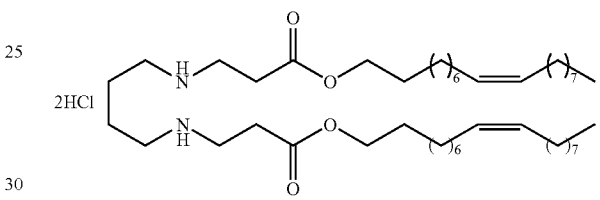

The ester 5 (n=4, R=oleyl; 13.0 g, 13.9 mmol) was dissolved in CH$_2$Cl$_2$ (70 mL) and treated with 4M HCl in EtOAc (140 mL). The resulting mixture was stirred at rt. for 2 h, then the solvent was removed in vacuo and the residue was triturated with anhydrous diethyl ether (150 mL) to afford a solid which was dried in vacuo to afford bis hydrochloride 6 as a white powder (10.23 g, 91%).

Rf$_{Silica}$: 0.46 (MeOH-0.88NH$_3$ 97:3). LC-MS (ESI): t$_R$=8.07 min (m/z=733.6 [M+H$^+$]).

Description 6: General Procedure to Prepare Surfactants (8a-d)

The N-terminal-protected amino acid (0.41 mmol, 2.6 eq.), HCTU (168 mg, 0.41 mmol, 2.6 eq.), and diisopropylethylamine (0.19 mL, 1.10 mmol, 7.0 eq.) were added to a solution of the amine hydrochloride 6 (n=4, R=oleyl; 150 mg, 0.156 mmol) in DMF-CH$_2$Cl$_2$ [1:1] (4.0 mL). The mixture was stirred at rt. under N$_2$ for 18 h and then the mixture was concentrated to low volume and EtOAc (30 mL) was added. The organic solution was washed successively with 5% aqueous KHSO$_4$ solution (3×8 mL), 5% aqueous K$_2$CO$_3$ solution (3×8 mL) and brine (3×10 mL), then dried (Na$_2$SO$_4$) and concentrated in vacuo. The residue was purified by reverse phase column chromatography eluting eluting with a solvent gradient of MeOH (50-100%) in water and then by silica gel column chromatography eluting with a solvent gradient of EtOAc (20-40%) in hexane. The residue was dissolved in EtOAc (2.0 mL) and 5.0N HCl in EtOAc (3.0 mL) was added. The resulting mixture was stirred at rt. for 2 h and then concentrated in vacuo and the solid residue triturated with diethyl ether (5.0 mL) to afford the surfactants 8a-d as white powders (75-93%).

Example 1 (8a)

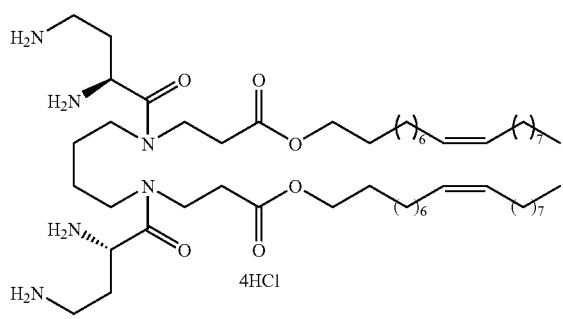

LC-MS (ESI): $t_R$=12.18 min (m/z=933.8 [M+H]$^+$ (100%)); HRMS (ESI) m/z calcd ($C_{54}H_{105}N_6O_6$) 933.8096, found 933.8096 [M+H]$^+$.

Example 2 (8b)

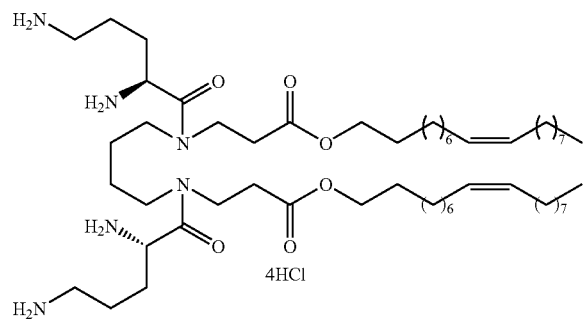

LC-MS (ESI): $t_R$=12.15 min (m/z=961.8 [M+H]$^+$ (100%)); HRMS (ESI) m/z calcd ($C_{56}H_{109}N_6O_6$) 961.8409, found 933.8400 [M+H]$^+$.

Example 3 (8c)

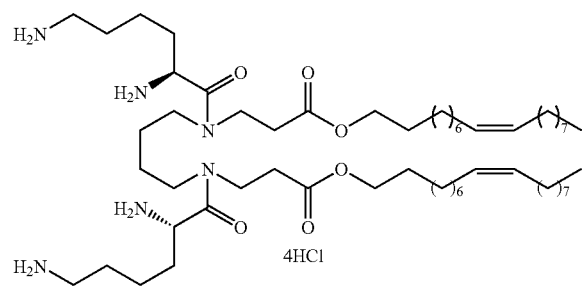

LC-MS (ESI): $t_R$=12.18 min (m/z=989.9 [M+H]$^+$ (100%)); HRMS (ESI) m/z calcd ($C_{58}H_{113}N_6O_6$) 989.8722, found 989.8718 [M+H]$^+$.

Example 4 (8d)

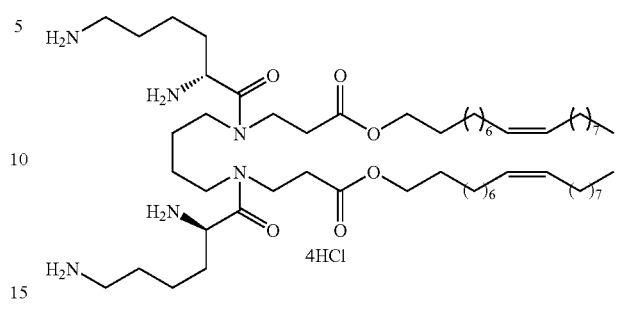

LC-MS (ES): $t_R$=12.20 min (m/z=989.9 [M+H]$^+$ (100%)); HRMS (ESI) m/z calcd ($C_{58}H_{113}N_6O_6$) 989.8722, found 989.8729 [M+H]$^+$.

Example 5

Transfection of Recombinant Plasmid Expressing GFP into Cells Using Ester-linked Surfactant Compounds Transfection studies were performed using the adherent cell line CHO-K1, CV1, HepG2, 1321N1 and NIH3T3 cells. Complete medium consisted of F12 (for CHO-K1), and DMEM (for CV1, HepG2, 1321N1 and NIH3T3) medium supplemented with 10% v/v foetal bovine serum and 1×L-Glutamine. All media and supplements were obtained from Life Technologies.

In Vitro Gene Transfection

Cells were seeded into tissue culture treated 96-well plates (Costar) 16-18 hours prior to transfection at an approximate density of 2×10$^4$ cells/well. A 0.025 µg/µl plasmid solution was prepared in Optimem. The plasmid used was pCMV-eGFP obtained from Clontech. The ester-linked surfactant compound was dissolved in Optimem as a 10× concentrate so as to achieve a final concentration of 20, 10, 5 and 2.5 µg/ml in the final reaction mixture. 10 µL of the ester-linked surfactant compound was mixed with 10 µl of the plasmid for each well. The complex was incubated at room temperature for 10 minutes. The medium was removed from the cells in the plate and they were washed once with 100 µl PBS. The complex (20 µl) was added to each well and then 80 µl Optimem (serum-free) or growth medium (serum) was added to make a final volume of 100 µl. In the serum-free protocol, the plate was then incubated for 6 hours at 37° C. and the medium was then removed and fresh complete medium was added to each well and incubation continued for a further 18 hours. In the serum protocol, the plate was incubated for 24 h at 37° C.

Reporter gene assays were performed according to the manufacturer's guidelines (Roche Diagnostics). The medium was removed from the plate and the cells were washed once with 100 µl PBS. 100 µl reporter lysis buffer (50 mM HEPES pH 7.5, 2 mM EDTA, 0.05% triton×100, 2 mM DTT) was then added to each well. The plate was then placed at −80° C. for 15 min and subsequently allowed to thaw at room temperature. Fluorescence was then measured using a standard plate reader (Tecan Ultra, Tecan) with excitation wavelength 485 nm and emission wavelength 520 nm.

The results are shown in FIGS. 3 (CHO-K1), 4 (HepG2), 5 (CV-1), 6 (1321N1) and 7 (NIH-3T3). The results show that all 3 ester gemini compounds tested were effective at transfecting the GFP plasmid into CHO-K1 cells, although not at efficiencies greater than Lipofectamine 2000. However in HepG2 cells all 3 test gemini compounds were, at the optimum concentration, more effective than Lipofectamine 2000 at 5 ug/ml.

In CV-1 cells the gemini compound of example 1 was superior at 10 and 20 ug/ml compared to Lipofectamine 2000 at all concentrations. The gemini compounds of examples 3 and 4 appeared to transfect CV-1 cells less effectively than that of example 1, but at a level comparable with Lipofectamine 2000.

With regard 1321N1 cells the gemini compounds of examples 1 and 2 were nearly 5 and 6 fold, respectively, more effective than Lipofectamine 2000. In both these cases the most effective concentration of the gemini compound was found to the lowest concentration tested, that is 2.5 ug/ml. The gemini compound of example 4 was not effective in transfecting 1321N1 cells.

All gemini compounds tested with NIH-3T3 cells were more effective than Lipofectamine 2000 at most concentrations tested. Example 4 showed the best effect.

These results show, in particular the results with 1321N1 and NIH-3T3 cells, that for each cell type there is an optimum gemini compound for high-efficiency transfection. Thus for 1321N1 cells both the compound of example 1 and that of example 2 are highly effective transfection agents, whereas the compound of example 4 was not effective at all. In contrast the compound of example 4 was found to be highly effective for transfecting NIH-3T3 cells whereas the compound of examples 1 and 2 were significantly less effective.

Thus, using the protocols detailed in this example the skilled person can easily determine by simple experimentation which ester gemini compound, whether one exemplified herein or a compound not exemplified but which can be made according to the synthetic protocols described above, is most suitable for the transfection of any given cell-line.

Example 6

Transfection of siRNA into Cells Using Ester-linked Surfactant Compounds

Knockdown studies were performed using the adherent cell lines A549, CV1 and Caco2. Complete medium consisted DMEM (for A549 and CV1) and EMEM (for Caco2) medium supplemented with 10% v/v foetal bovine serum and 1× L-Glutamine. All media and supplements were obtained from Life Technologies.

In Vitro siRNA Transfection

Cells were seeded into tissue culture treated 96-well plates (Costar) 16-18 hours prior to transfection at an approximate density of $2\times10^4$ cells/well. A 1 µM solution of siRNA (targeting JNK1 or non-targeting control) purchased from Dharmacon was prepared in Optimem. The ester-linked surfactant was dissolved in Optimem as a 10× concentrate so as to achieve a final concentration of 5 µg/ml in final the reaction mixture. The commercial reagent lipofectamine 2000 was used at a final concentration of 2.5 µg/ml, siLentFect at 1 µg/ml and X-tremeGene at 0.5 µl/well. A 10 µl sample of the ester-linked surfactant (commercial) lipid was mixed with 10 µg of the siRNA for each well. The complex was incubated at room temperature for 10 minutes. The medium was removed from the cells in the plate and they were washed once with 100 µl PBS. The complex (20 µl) was added to each well and then 80 µl growth medium was added to make a final volume of 100 µl. and the plate was incubated for 24 h at 37° C. At this time point the cells were washed once using 100 µl PBS and then lysed in 100 µl RNA lysis buffer (Promega). Standard quantitative RT-PCR (Taqman) was carried out to determine the relative abundance of JNK1 compared to the housekeeping gene GAPDH in both JNK1 siRNA targeted and non-targeted cells. The degree of knockdown was expressed as a ratio of treated (JNK1) copies of Jnk1 to control (non-targeted) copies of JNK1.

The results are shown in FIG. 2. It can be seen that in all 3 cell types tested the level of Jnk1 was significantly reduced when siRNA duplexes were transfected into the cells using the gemini compounds of the present invention compared with non-targetted control cells. The level of expression of Jnk1 was between 70 and 85% lower than the levels observed in the untreated cells. A similar knockdown effect was seen in cells where Lipofectamine 2000 was used to transfect in the siRNA duplexes, but in all cell types the effect was less marked that that observed with the ester gemini compounds (between 65 and 79% lower than the untreated controls).

All publications, including but not limited to patents and patent applications, cited in this specification are herein incorporated by reference as if each individual publication were specifically and individually indicated to be incorporated by reference herein as though fully set forth.

Figure 1:
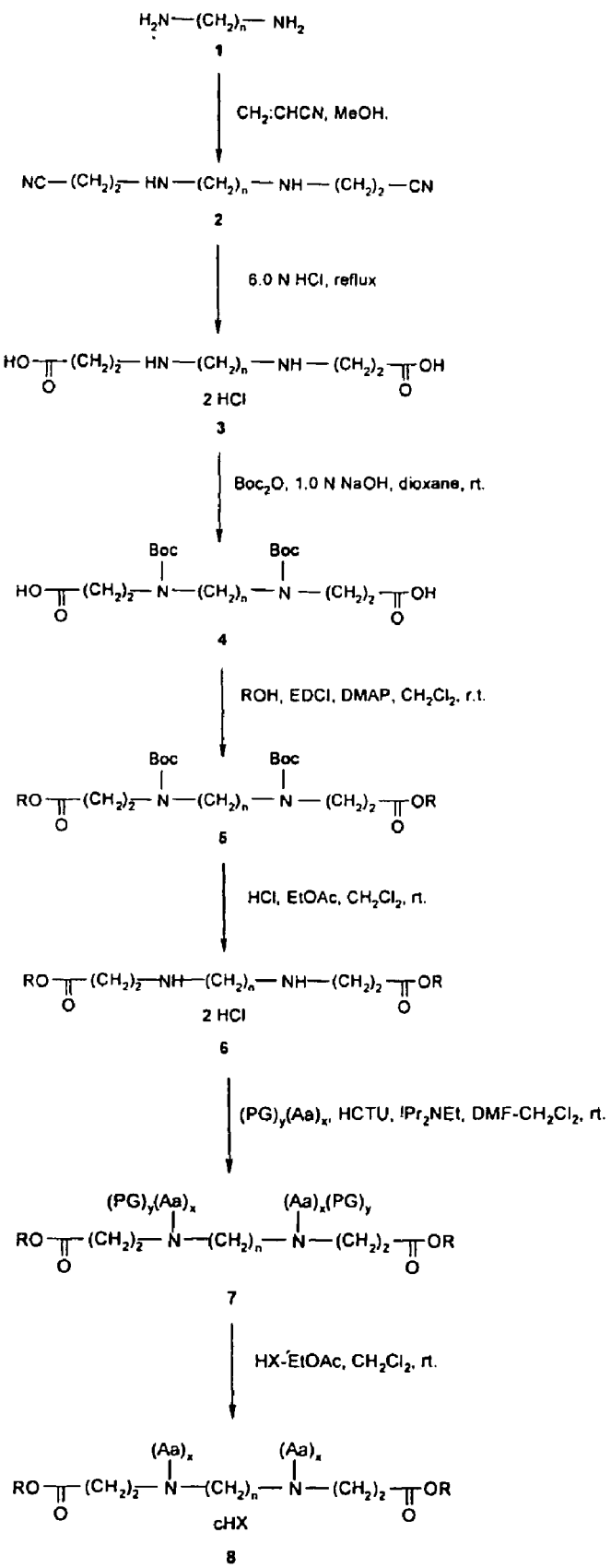
FIG. 1 shows a general scheme for the synthesis of an ester-linked surfactant.
Figure 2:
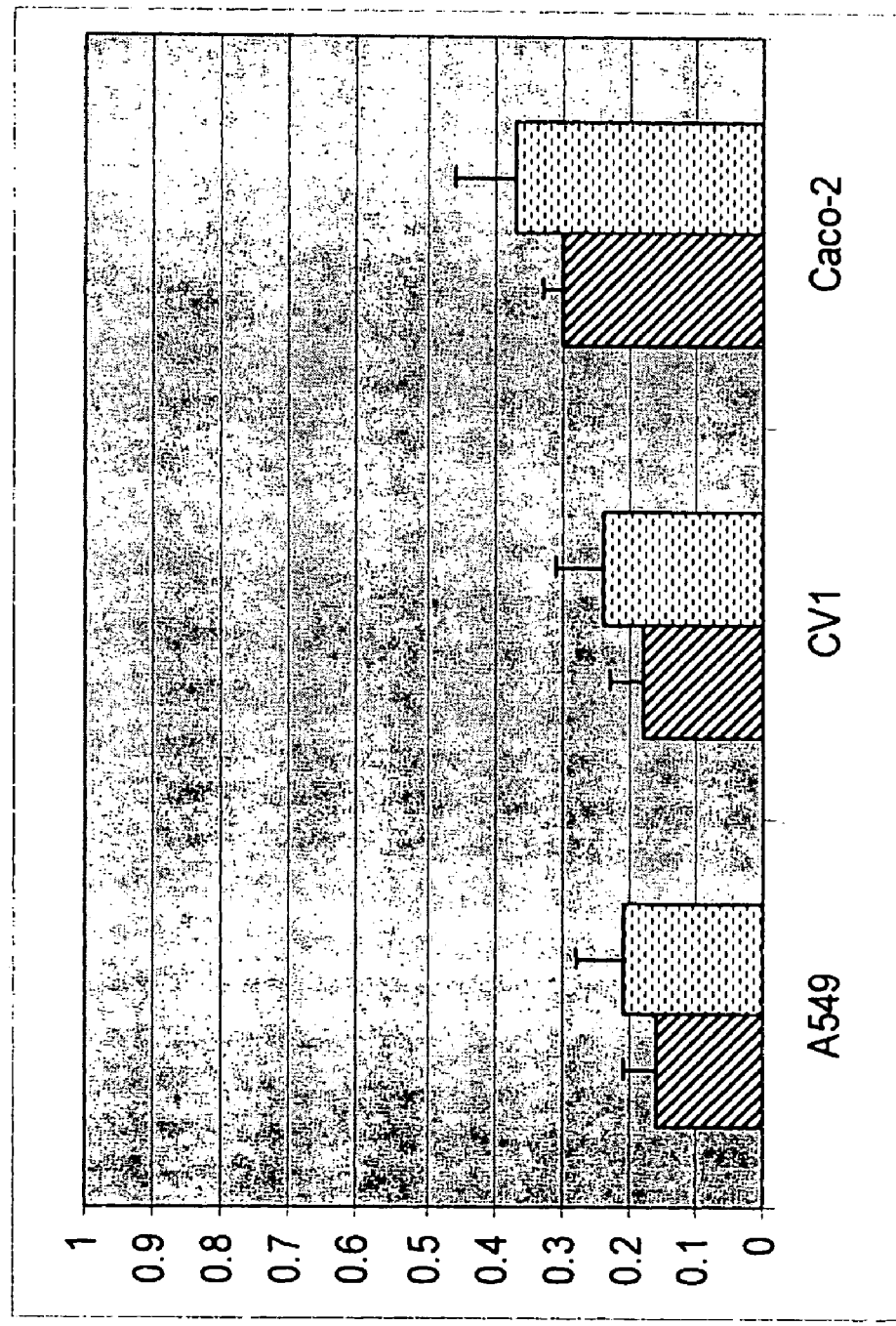
FIG. 2 shows knockdown of Jnk1 expression using siRNA duplexes. The cell type is indicated along the X axis and the ratio of treated (JNK1) copies of Jnk1 to control (non-targeted) copies of JNK1 is indicated along the Y axis. The diagonally hatched bars relate to cells treated with the ester gemini of example 1 and the dashed-horizontal shading relates to the cells when treated with Lipofectamine 2000 (example 6).
Figure 3:
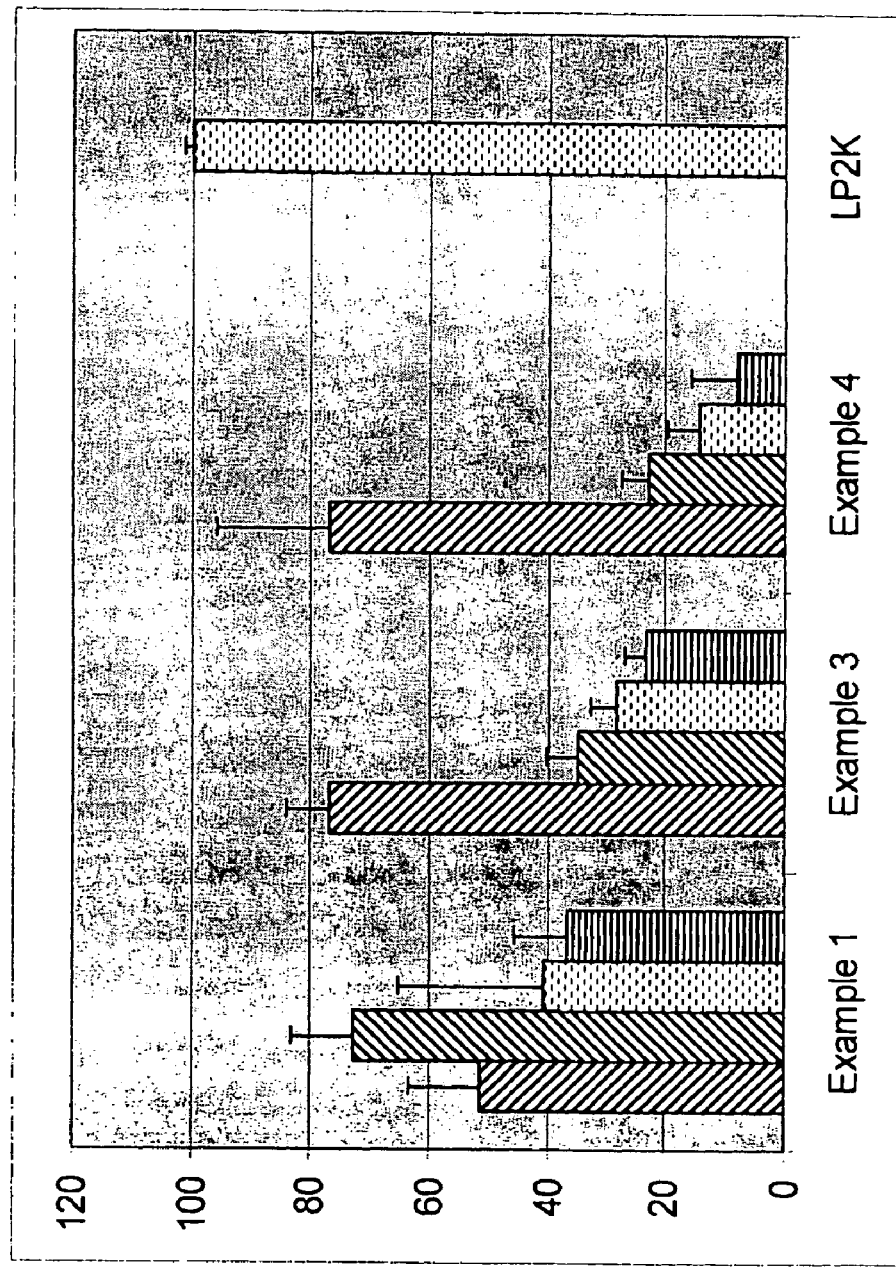
FIGS. 3 and 4 show green fluorescent protein (GFP) expression in cells after transfection of pCMV-eGFP, a GFP-expressing plasmid, into CHO-K1 cells (FIG. 3) and HepG2 cells (FIG. 4) using ester geminis. The level of GFP expression in the cells is shown as a % of the level of expression achieved with Lipofectamine 2000. The data is shown in 3 blocks of 4 bars, each block relating to a specific ester gemini. The first block of 4 bars shows transfection efficiency using the ester Gemini of example 1; the second block example 3 and the third block example 4. The Gemini was used at four concentrations: 20 ug/ml (top left to bottom right hatching); 10 ug/ml (top right to bottom left hatching), 5 ug/ml (dashed-horizontal lines) and 2.5 ug/ml (solid horizontal lines). Lipofectamine is shown as a single bar (LP2K) at 5 ug/ml.
Figure 4:
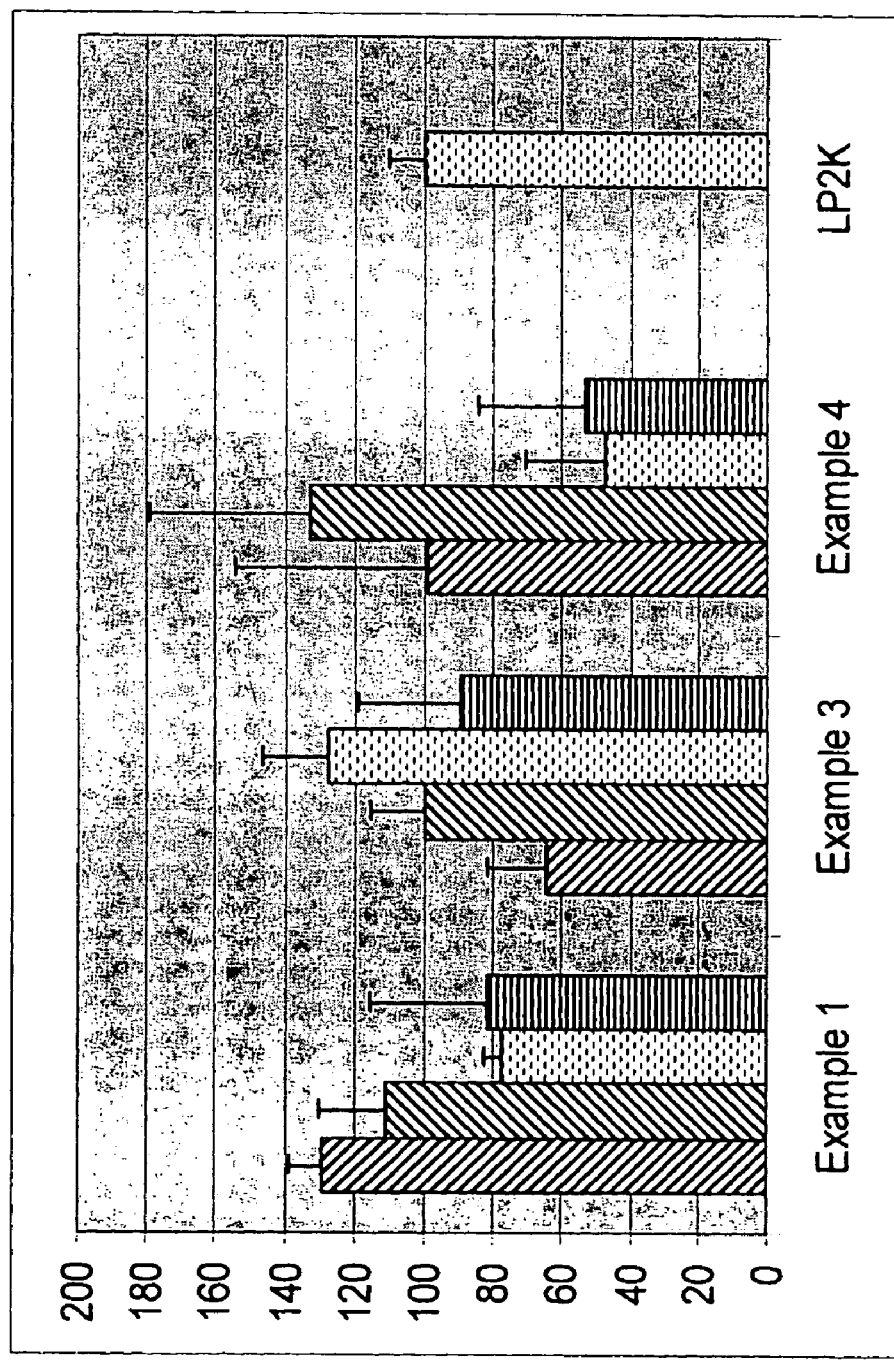
Figure 5:
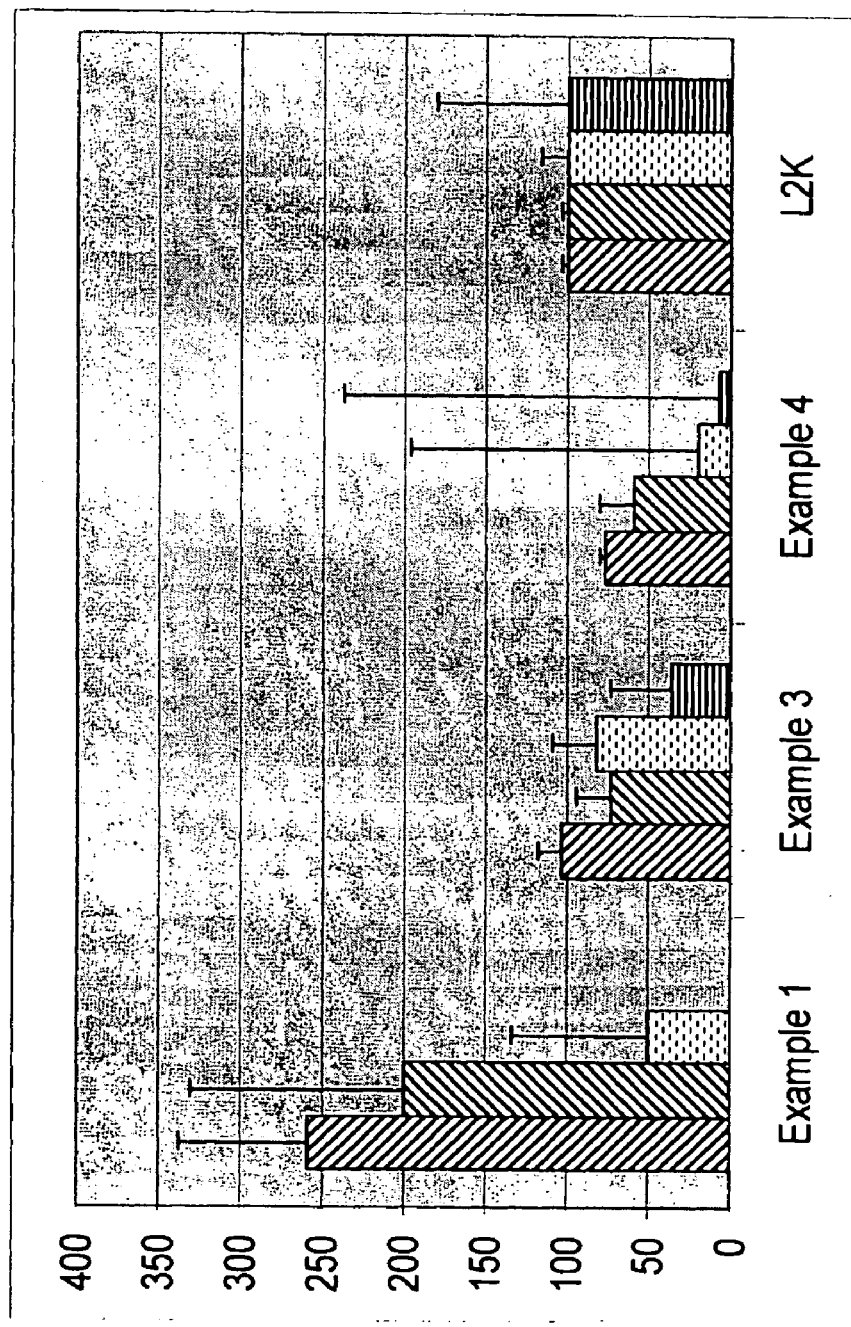
FIGS. 5, 6 and 7 show show green fluorescent protein (GFP) expression in cells after transfection of pCMV-eGFP, a GFP-expressing plasmid, into CV-1 cells (FIG. 5), 1321N1 cells (FIG. 6) and NIH-3T3 cells (FIG. 7) using ester geminis. The level of GFP expression in the cells is shown as a % of the level of expression achieved with Lipofectamine 2000. The data is shown in 4 blocks of 4 bars, each block relating to a specific ester gemini. The first block of 4 bars shows transfection efficiency using the ester Gemini of example 1; the second block example 3, the third block example 4 and the fourth block Lipofectamine 2000 (L2K). The ester geminis and Lipofectamine 2000 were used at four concentrations: 20 ug/ml (top left to bottom right hatching); 10 ug/ml (top right to bottom left hatching), 5 ug/ml (dashed-horizontal lines) and 2.5 ug/ml (solid horizontal lines).
Figure 6:
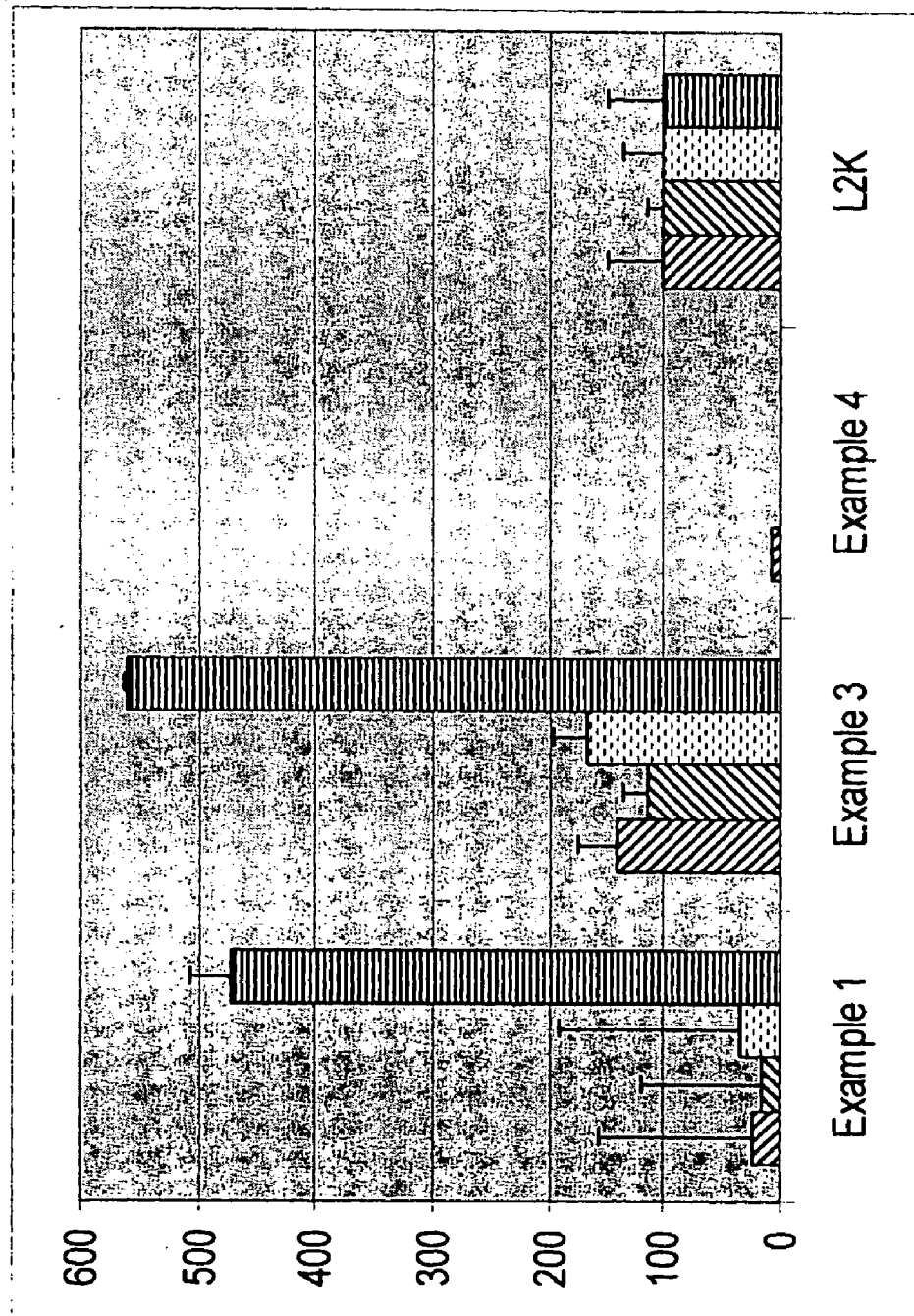
Figure 7:
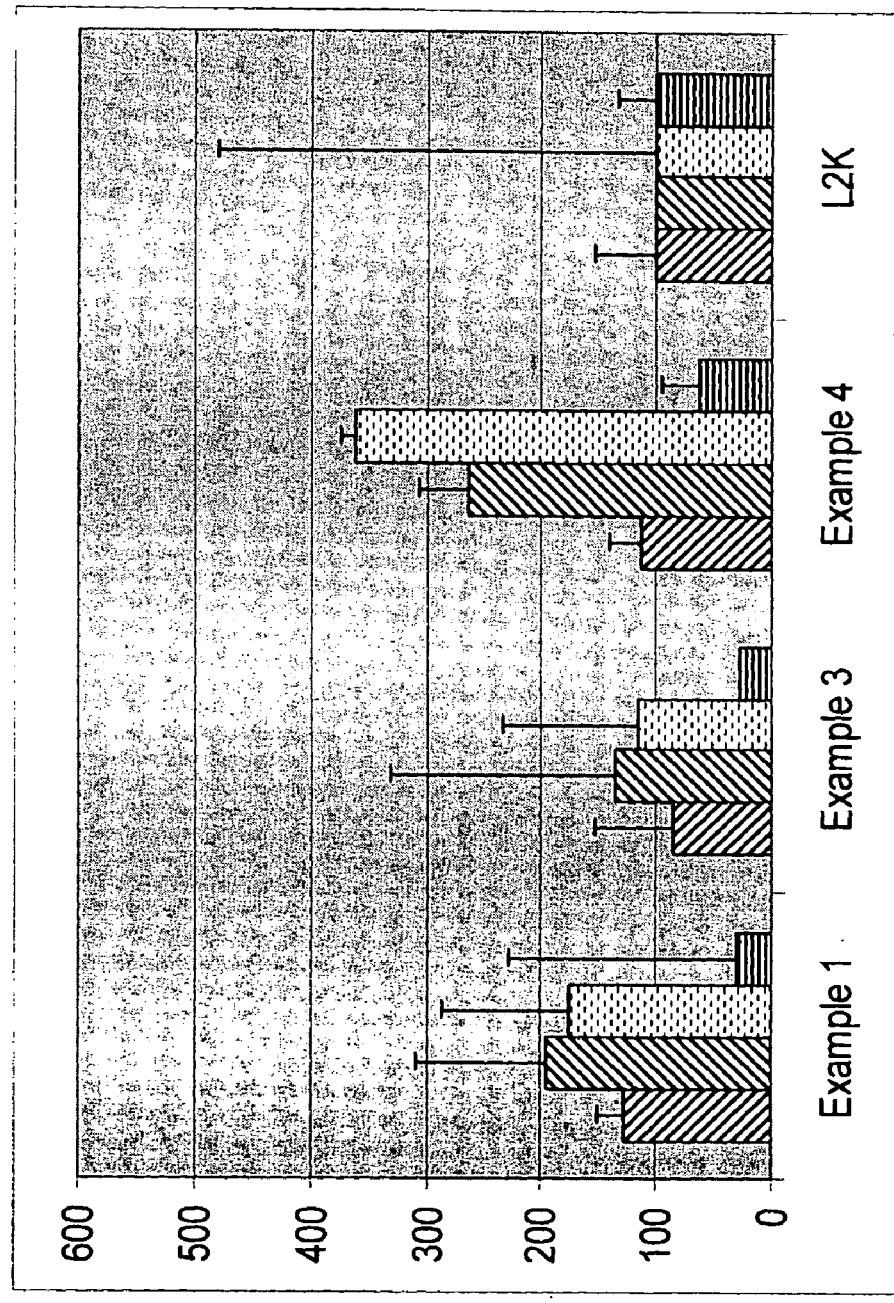

The invention claimed is:

1. A compound having the general structure of formula (I):

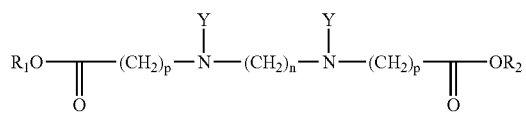

where each Y is independently (Aa)$_x$ where (Aa) is a basic amino acid residue linked to each N in formula (I) by means of a peptide bond between each N of formula (I) and the carboxy group on the amino acid residue; and x is 1 to 6;

$R_1$ and $R_2$, which may be the same or different, are saturated or unsaturated, linear or branched hydrocarbon chains of up to 24 carbon atoms;

n is 1 to 10; and p is 1 to 6;

or a pharmaceutically acceptable salt thereof.

2. A compound according to claim 1 in which n is 4.

3. A compound according to claim 2 in which p is 2 and x is 1, 2, or 3.

4. A compound according to claim 3 in which the basic amino acid residue (Aa) is a residue of lysine, ornithine, diaminobutyric acid or diaminopropionic acid; $R^1$ and $R^2$, which may be the same or different, are saturated or unsaturated, linear or branched hydrocarbon chains of from 10 to 24 carbon atoms; and x is 1 or 2.

5. A compound according to claim 4 in which x is 1.

6. A compound according to claim 1 in which $R_1$ and $R_2$ are each:

—(CH$_2$)$_{10}$CH$_3$
—(CH$_2$)$_{12}$CH$_3$
—(CH$_2$)$_{14}$CH$_3$
—(CH$_2$)$_{16}$CH$_3$
—(CH$_2$)$_{18}$CH$_3$
—(CH$_2$)$_{20}$CH$_3$
—(CH$_2$)$_7$CH═CH(CH$_2$)$_7$CH$_3$ natural mixture
—(CH$_2$)$_7$CH═CH(CH$_2$)$_5$CH$_3$ natural mixture
—(CH$_2$)$_7$CH═CH(CH$_2$)$_5$CH$_3$ Cis
—(CH$_2$)$_7$CH═CH(CH$_2$)$_7$CH$_3$ Cis
—(CH$_2$)$_7$CH═CH(CH$_2$)$_5$CH$_3$ Trans
—(CH$_2$)$_7$CH═CH(CH$_2$)$_7$CH$_3$ Trans
—(CH$_2$)$_7$CH═CHCH$_2$CH═CH(CH$_2$)$_4$CH$_3$
—(CH$_2$)$_7$(CH═CHCH$_2$)$_3$CH$_3$
—(CH$_2$)$_3$CH═CH(CH$_2$CH═CH)$_3$(CH$_2$)$_4$CH$_3$
—(CH$_2$)$_7$CHCH(CH$_2$)$_7$CH$_3$
—CH$_2$CH(CH$_3$)[CH$_2$CH$_2$CH$_2$CH(CH$_3$)]$_3$CH$_3$
or —(CH$_2$)$_{22}$CH$_3$.

7. A compound according to claim 6 in which $R_1$ and $R_2$ are each:

(CH$_2$)$_7$CH═CH(CH$_2$)$_7$CH$_3$ natural mixture,
(CH$_2$)$_7$CH═CH(CH$_2$)$_7$CH$_3$ Cis or
(CH$_2$)$_7$CH═CH(CH$_2$)$_7$CH$_3$ Trans.

8. A compound of formula:

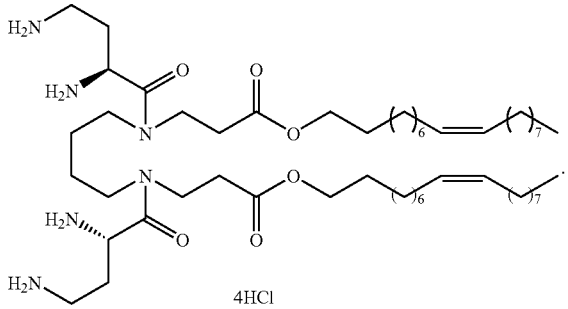

9. A compound of formula:

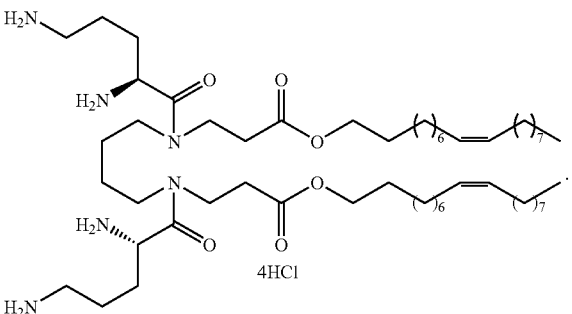

10. A compound of formula:

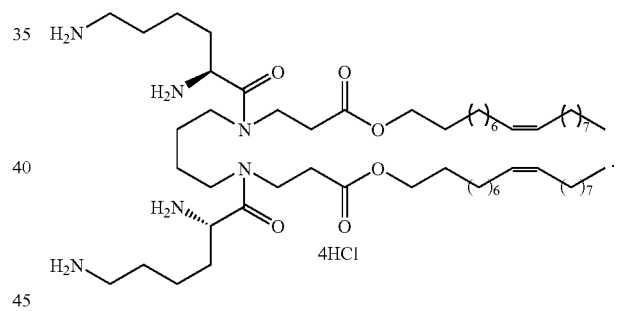

11. A compound of formula:

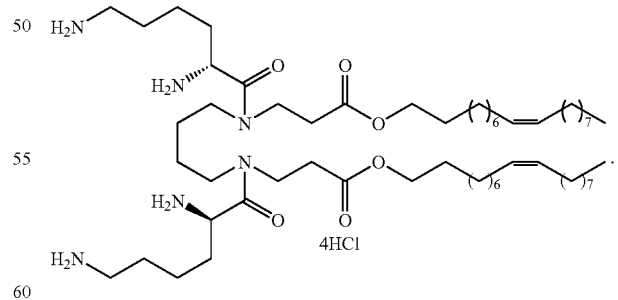

12. A method of transfecting polynucleotides into cells in vivo for gene therapy, which method comprises administering a compound of claim 1 together with, or separately from, a gene therapy vector.

* * * * *